United States Patent
Laemmle et al.

(10) Patent No.: US 8,703,429 B2
(45) Date of Patent: *Apr. 22, 2014

(54) COMPOSITION EXHIBITING A VON WILLEBRAND FACTOR (VWF) PROTEASE ACTIVITY COMPRISING A POLYPEPTIDE CHAIN WITH THE AMINO ACID SEQUENCE AAGGILHLELLV

(75) Inventors: Bernhard Laemmle, Bolligen (CH); Helena Elisabeth Schaller-Gerritsen, Muri (CH); Miha Furlan, Bern (CH); Peter Turecek, Klosterneuburg (AT); Hans-Peter Schwarz, Vienna (AT); Friedrich Scheiflinger, Vienna (AT); Gerhard Antoine, Gross-Enzersdorf (AT); Randolf Kerschbaumer, Klosterneuburg (AT); Luigina Tagliavacca, Milan (IT); Klaus Zimmermann, Pressbaum (AT)

(73) Assignee: Baxter Innovations GmbH, Vienna (AT)

( * ) Notice: Subject to any disclaimer, the term of this patent is extended or adjusted under 35 U.S.C. 154(b) by 579 days.

This patent is subject to a terminal disclaimer.

(21) Appl. No.: 12/171,934

(22) Filed: Jul. 11, 2008

(65) Prior Publication Data

US 2009/0017467 A1     Jan. 15, 2009

Related U.S. Application Data

(60) Continuation of application No. 11/166,288, filed on Jun. 23, 2005, now Pat. No. 7,501,117, which is a division of application No. 09/833,328, filed on Apr. 12, 2001, now Pat. No. 6,926,894, which is a continuation-in-part of application No. 09/721,254, filed on Nov. 22, 2000, now abandoned.

(51) Int. Cl.
 *G01N 33/53* (2006.01)
 *C12N 9/64* (2006.01)

(52) U.S. Cl.
 USPC .......................... 435/7.1; 435/226; 424/49.67

(58) Field of Classification Search
 None
 See application file for complete search history.

(56) References Cited

U.S. PATENT DOCUMENTS

| | | | |
|---|---|---|---|
| 6,579,723 B1 * | 6/2003 | Mitterer et al. | ............... 436/177 |
| 6,926,894 B2 | 8/2005 | Laemmle et al. | |
| 2001/0049106 A1 | 12/2001 | Buckbinder et al. | |

OTHER PUBLICATIONS

Furlan M. et al. "Partial Purification and Characterization of a Protease From Human Plasma Cleaving von Willebrand Factor to Fragments Produced by In Vivo Proteolysis." *Blood* (May 15, 1996), 87(10):4223-4234.

Gerritsen, H. et al. "Partial amino acid sequence of purified von Willebrand factor-cleaving protease." *Blood* (Sep. 15, 2001), 98(6):1654-1661.

Zheng, X. et al. "Structure of von Willebrand Factor—cleaving Protease (ADAMTS13), a Metalloprotease Involved in Thrombotic Thrombocytopenic Purpura." *J. Biol. Chem.* (Nov. 2, 2001), 276(44):41059-41063.

NCBI Entrez Nucleotide Sequence Report: NM_139025, http://www.ncbi.nlm.nih.gov/entrez/viewer.fcgi?db=nucleotide&val=21265033.

NCBI Entrez Nucleotide Sequence Report: NM_139026, http://www.ncbi.nlm.nih.gov/entrez/viewer.fcgi?db=nucleotide&val=21265042.

NCBI Entrez Nucleotide Sequence Report: NM_139027, http://www.ncbi.nlm.nih.gov/entrez/viewer.fcgi?db=nucleotide&val=21265045.

NCBI Entrez Nucleotide Sequence Report: NM_139028, http://www.ncbi.nlm.nih.gov/entrez/viewer.fcgi?db=nucleotide&val=21265048.

* cited by examiner

*Primary Examiner* — Richard Hutson
(74) *Attorney, Agent, or Firm* — Kilpatrick Townsend & Stockton LLP

(57) ABSTRACT

The invention relates to vWF cleaving entities having a molecular weight of 180 kD, 170 kD, 160 kD, 120 kD or 110 kD and an N-terminal amino acid sequence of AAG-GILHLELLV, vWF cleaving complexes and methods for their production.

6 Claims, 5 Drawing Sheets

3. Purification Step

Pooled Eluate from Step 2

↓

Affinity Chromatography

Heparin-Sepharose 5ml

↓

*Dialysis*

↓

Anion Exchange Chromatography

High Q Support® 5 ml

↓

Gel Filtration

Sephacryl ® S-300 HR 500 ml

↓

Elution of vWF Protease with NaCl 0.5 M

FIG. 1

Optional: 4. Purification Step

Pooled Eluate from Step 3

↓

| Affinity Chromatography |

Anti-$\alpha_2$-Macroglobulin-column 1ml

↓ and/or optional

↓

| Affinity Chromatography |

Anti-Clusterin column

```
gctgcaggcggcatcctacacctggagctgctggtggccgtgggccccgatgtc
 A  A  G  G  I  L  H  L  E  L  L  V  A  V  G  P  D  V
ttccaggctcaccaggaggacacagagcgctatgtgctcaccaacctcaacatcggggca
 F  Q  A  H  Q  E  D  T  E  R  Y  V  L  T  N  L  N  I  G  A
gaactgcttcgggacccgtccctgggggctcagtttcgggtgcacctggtgaagatggtcat
 E  L  R  D  P  S  L  G  A  Q  F  R  V  H  L  V  K  M  V  I
tctgacagagcctgagggtgccccaaatatcacagccaacctcacctcgtccctgctgagc
 L  T  E  P  E  G  A  P  N  I  T  A  N  L  T  S  S  L  L  S
gtctgtgggtggagccagaccatcaaccctgaggacgacacggatcctggccatgctgac
 V  C  G  W  S  Q  T  I  N  P  E  D  D  T  D  P  G  H  A  D
ctggtcctctatatcactaggtttgacctggagttgcctgatggtaaccggcaggtgcgg
 L  V  L  Y  I  T  R  F  D  L  E  L  P  D  G  N  R  Q  V  R
ggcgtcacccagctgggcggtgcctgctccccaacctggagctgcctcattaccgaggac
 G  V  T  Q  L  G  G  A  C  S  P  T  W  S  C  L  I  T  E  D
actggcttcgacctgggagtcaccatt
 T  G  F  D  L  G  V  T  I
```

Fig. 2

COMPOSITION EXHIBITING A VON WILLEBRAND FACTOR (VWF) PROTEASE ACTIVITY COMPRISING A POLYPEPTIDE CHAIN WITH THE AMINO ACID SEQUENCE AAGGILHLELLV

This application is a continuation application of U.S. application Ser. No. 11/166,288, filed Jun. 23, 2005, which is a divisional application of U.S. application Ser. No. 09/833,328, filed Apr. 12, 2001 (now U.S. Pat. No. 6,926,894, issued Aug. 9, 2005), which is a continuation-in-part of U.S. application Ser. No. 09/721,254 filed on Nov. 22, 2000 (abandoned); the disclosures of which are incorporated by reference herein.

FIELD OF THE INVENTION

The invention relates to a vWF protease-containing composition which includes a polypeptide comprising the amino acid sequence AAGGILHLELLV, as well as to nucleotide sequences coding for such a polypeptide. It further relates to methods for increasing the stability of the vWF protease.

BACKGROUND OF THE INVENTION vWF is a glycoprotein circulating in plasma as a series of multimers ranging in size from about 500 to 20,000 kD. Multimeric forms of vWF are composed of 250 kD polypeptide subunits linked together by disulfide bonds. vWF mediates the initial platelet adhesion to the subendothelium of a damaged vessel wall, though only the largest multimers appear to exhibit haemostatic activity. Such vWF multimers having large molecular masses are stored in the Weibel Palade bodies of endothelial cells, and it is believed that endothelial cells secrete these large polymeric forms of vWF. Those forms of vWF which have a low molecular weight (low molecular weight or LMW vWF) are believed to arise from proteolytic cleavage of the larger multimers.

A small portion of the vWF present in normal plasma circulates as 189, 176 and 140 kD fragments resulting from proteolytic degradation of vWF in vivo, the 140 kD fragment being derived from the N-terminal region, and the 176 kD fragment from the C-terminal region of the subunit. When LMW forms of vWF are isolated from normal human plasma and subjected to SDS-PAGE (polyacrylamide gel electrophoreses) after disulfide reduction, an unusually high portion of vWF fragments are found. This finding is compatible with the view that LMW forms of vWF have been partially or predominantly derived from large multimers by proteolytic degradation.

The proteolytic degradation of vWF is a physiological process in healthy individuals, yet in patients suffering from von Willebrand disease (vWD) type 2A it may be accelerated, and as a consequence these patients lack the vWF multimers with the largest molecular masses. A lack of large vWF multimers and an increased level of proteolytic fragments are also observed in acquired von Willebrand disease (vWD) associated with myeloproliferation syndrome, indicating increased in vivo proteolysis in this condition as well.

In patients with thrombotic thrombocytopenic purpura (TTP), on the other hand, unusually large vWF multimers are detected, and increased vWF binding to platelets has been demonstrated in these patients (Moake et al., New Engl. J. Med., 1982, 307, pp. 1432-1435). Familial TTP is associated with a severe congenital deficiency of vWF protease, while the presence of vWF-cleaving proteases inhibiting autoantibodies has been observed in patients with non-familial TTP.

The large multimers of vWF associated with TTP normally disappear after a patient is transfused with normal fresh frozen plasma. Presently, plasma exchange is the most important treatment for UP, although significant side effects have been reported with this therapy. The existence of a severe congenital deficiency of vWF protease has been established in patients with familial TTP and the presence of a vWF-cleaving protease inhibiting autoantibodies has been observed in patients with non-familial TTP.

Several proteases have been shown to be able to cleave vWF, thereby impairing its binding affinity for platelets. However, in vitro the cleavage of vWF with these proteases in each case results in cleavage products different from the fragments derived from in vivo cleavage.

Thus, for example, while plasmin is capable of cleaving several peptide bonds in vWF, plasmin-treated vWF retains a high molecular weight core region retaining about 70% of its platelet agglutinating activity (determined as ristocetin cofactor). A 34 kD peptide is split from the N-termini of individual vWF subunits in the early stages of plasmin treatment, and epitope mapping of such plasmin-induced fragments show that these fragments originated from regions of the vWF subunit that are different from the vWF fragments present in circulating plasma.

Porcine pancreatic elastase and various serine proteases released from human leukocytes have also been shown to degrade vWF proteolytically with a resultant loss of large multimers. Epitope mapping of the degradation products again indicates that these fragments also differ from those present in normal plasma and in vWD type 2A. In addition, a calpain-like protease released from human platelets has been shown to degrade large vWF multimers and to create vWF fragments similar to those observed in vivo.

SUMMARY OF THE INVENTION

We have isolated a composition exhibiting vWF protease activity that is capable of proteolytically processing vWF in a physiological manner. Said composition comprises at least one single peptide chain having a molecular weight between 190 kD and 100 kD as determined by SDS PAGE and comprises the sequence AAGGILHLELLV. This amino acid sequence is located at the N-terminus of the peptide chain. The composition comprising the sequence AAGGHILHLELLV can also be used for isolation, detection or purification of proteins, i.e. von Willebrand Factor.

Furthermore, an isolated polypeptide having a molecular weight between 190 kD and 100 kD according to SDS-PAGE and comprising the sequence AAGGILHLELLV is also provided. This sequence is preferably directly followed by the sequence AVG, which is preferably followed by the sequence

```
PDVFQAHQEDTERYVLTNLNIGAELLRDPSLGAQFRVHLVK

MVILTEPEGAPNITANLTSSLLSVCGWSQTINPEDDTDPGHADLVLYITR

FDLELPDGNRQVRGVTQLGGACSPTWSCLITEDTGFDLGVTI.
```

Another aspect of the present invention is a method of purifying von Willebrand factor comprising contacting a solution containing von Willebrand factor with a substrate comprising the amino acid sequence AAGGILHLELLV under conditions sufficient to bind von Willebrand factor to the substrate.

The present invention further comprises a method of treating thrombotic diseases using a polypeptide of the present invention, as shown in FIG. 2.

In addition, the present invention includes a method of processing recombinantly produced vWF through the use of the vWF protease of the present invention, in order to produce a vWF product.

BRIEF DESCRIPTION OF THE DRAWINGS

FIG. 2 shows the partial nucleotide sequence (SEQ ID NO:3) and amino acid sequence (SEQ ID NO:4) of the vWF protease of the present invention.

DETAILED DESCRIPTION OF THE INVENTION

Figure 1:
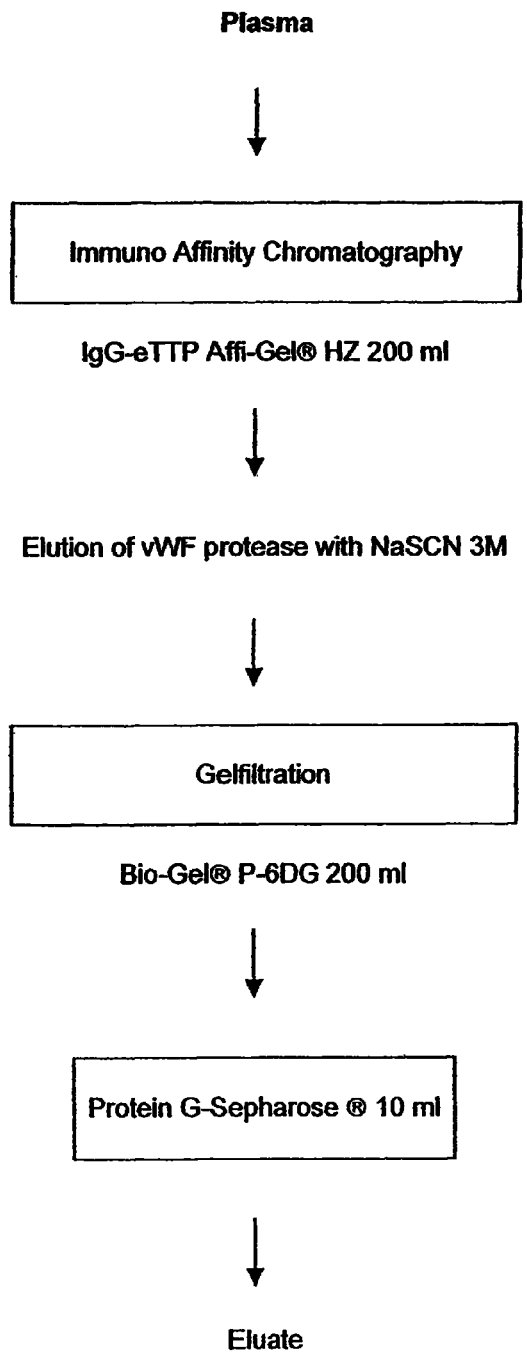
FIG. 1 shows the schematic purification scheme of the vWF protease containing composition of the present invention.
Figure 1:
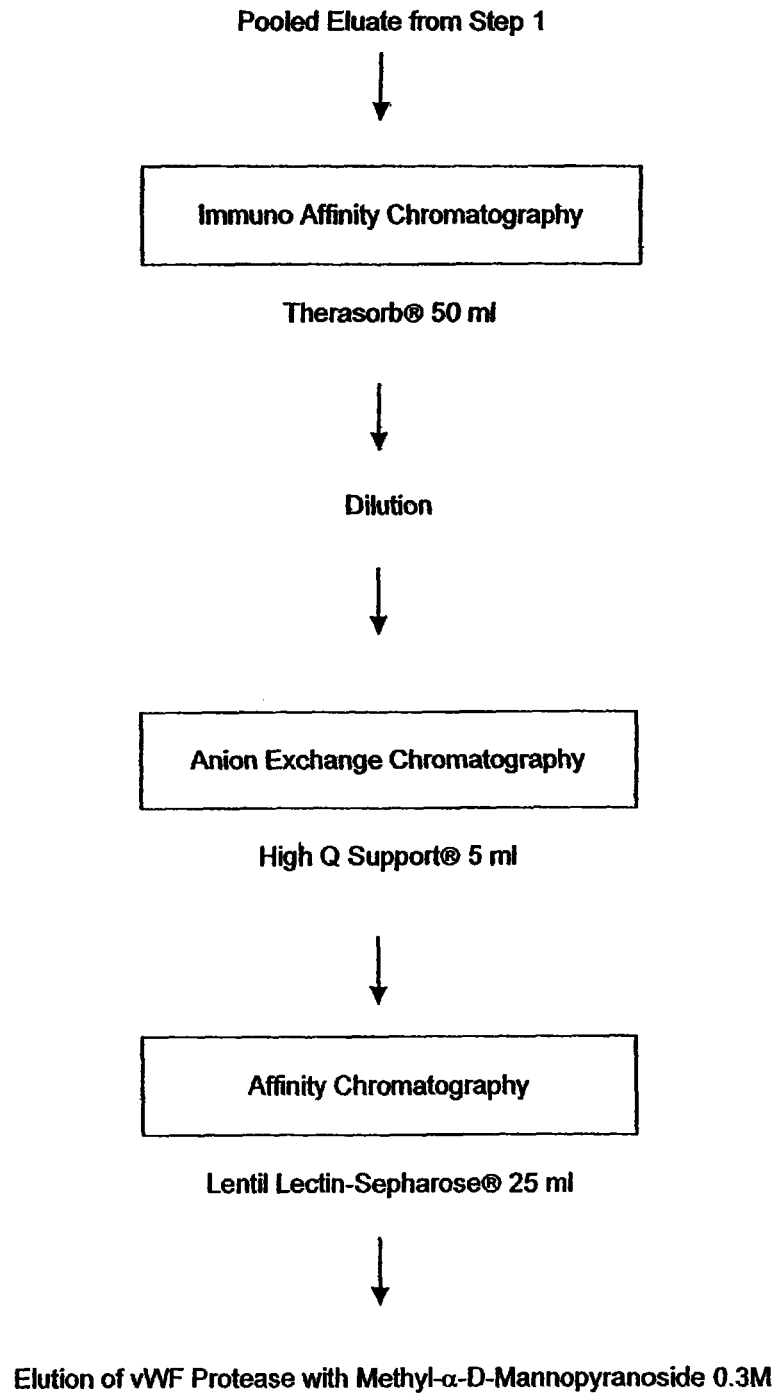
Figure 1:
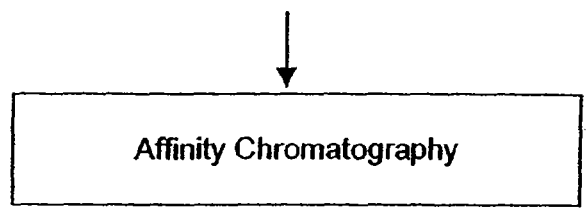
Figure 1:
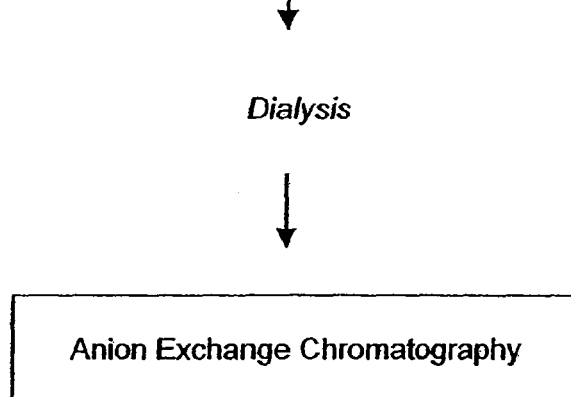

A composition is provided containing a vWF protease consisting of a polypeptide chain with an apparent molecular weight in SDS-PAGE of around 180 kD, around 170 kD, around 160 kD, around 120 kD, around 110 kD or mixtures of these chains, said chain comprising an amino acid sequence AAGGILHLELLV. Alternatively, this amino acid sequence can be directly followed by the amino acid sequence AVG. Furthermore, this sequence is followed by the sequence

```
PDVFQAHQEDTERYVLTNLNIGAELLRDPSLGAQFRVHL
VKMVILTEPEGAPNITANLTSSLLSVCG-
WSQTINPEDDTDPGHADLVLYITR-
FDLELPDGNRQVRGVTQLGGACSPTWSCLITEDTGFDLGVTI.
```

The SDS-PAGE was performed under reducing conditions. As is well known in the art, molecular weight determination using SDS PAGE results in the detection of apparent molecular masses, which may be different from the molecular masses of the native, non-denatured protein.

Based on a computer search of sequence homologies, the vWF protease according to the invention shows high homology to the group of disintegrin and metalloproteinases (ADAM). Members of this group share several distinct protein modules, including a protease domain, a disintegrin domain, a cysteine-rich region and an EGF repeat (Tang B L and Hong W., FEBS, 1999, 445, pp. 223-225). The nucleotide and amino acid sequence as shown in FIG. 2 comprises at least 4 exons of the protease portion of the vWF protease of the present invention.

Analysis of non-denatured material by mass spectrometry showed very broad peaks of high molecular weight. No prominent bands were identified. This finding is in agreement with appearance, in gel filtration experiments, of 80 kD bands close to the void volume of Sephacryl® S-300, suggesting that the proteins in this preparation tend to polymerize under physiologic conditions (a property of clusterin).

The AAGGILHLELLV sequence is located at the N-terminal region of the protein. Shortening of the peptide chain occurs at the C-terminus or via endoproteolytical cleavages. The composition according to the present invention contains a vWF cleaving protease that is expressed as a single chain protein.

Preferably, the composition according to the present invention further comprises $Ca^{2+}$, $Sr^{2+}$ and/or $Ba^{2+}$ ions. The preparation may comprise calcium ions in a concentration of about 1 to $10^6$ ions per polypeptide molecule with vWF protease activity. The preparation according to the present invention contains vWF protease activity in an essentially purified form. Preferably, the purified protease preparation from plasma contains between 0.001% and 1%, preferably 0.002% of the initial amount of plasma protein, and between 1% and 5%, preferably 2.3% of the initial enzyme activity, which has been partially inactivated during the purification procedure. Preferably, the purity is as high as the relative proportions of polypeptide chains with the vWF protease activity present in an amount of above 50%, especially above 80%, most preferred about 90%, of total protein compared to the vWF protease activity in plasma. Preferably, the preparation according to the present invention is essentially free of vWF or vWF fragments, i.e. having a vWF content of below 5%, preferably below the detection limit of an assay used to detect vWF.

The peptides containing the amino acid sequence AAG-GILHLELLV or AAGGILHLELLVAVG or AAG-GILHLELLVAVGPDVFQAHQEDTERYV-LTNLNIGAELLRD
PSLGAQFRVHLVKMVILTEPEGAPNI-TANLTSSLLSVCGWSQTINPEDDTDPGHADLVLYIT RFDLELPDGNRQVRGVTQLGGACSPTWS-CLITEDTGFDLGVTI or RRAAGGILHLELLV AVGPD-VFQAHQEDTERYVLTNLNIGAELL-RDPSLGAQFRVHLVKVILEPEGAITANL
TSSLLSVCGWSQTINPEDDTDPGHADLV-LYITRFDLELPDGNRQVRGVTQLGGACSPTWS CLIT-EDTGFDLGVTI can also be used as tool for detecting proteins binding to the vWF protease or target sites for ligand development for detecting, isolating and purifying proteins that bind to the vWF protease. Preferably the protein to be detected or purified is vWF.

These ligands can for example be peptides or peptidomimetics capable to bind proteins binding to the vWF protease or binding domains incorporated into antibodies or antibody derivatives (for example single chain antibodies, minianti-bodies, bispecific antibodies, diabodies etc.).

Furthermore, the peptide having the amino acid sequence AAGGILHLELLV or AAGGILHLELLVAVG or AAG-GILHLELLV AVGPDVFQAHQEDTERYVLTNLNI-GAELLRDPSLGAQFRVHLVKMVILTEPEGAPNITANL TSSLLSVCGWSQTINPEDDTDPGHADLV-LYITRFDLELPDGNRQVRGVTQLGGACSPTWS CLIT-EDTGFDLGVTI or RRAAGGILHLELLV AVGPD-VFQAHQEDTERYVLTNLNIGAELLRDPSLGAQFRVH-LVKMVILTEPEGAPNITANL TSSLLSVCGWSQTIN-PEDDTDPGHADLVLYITRFDLELPDGN-RQVRGVTQLGGACSPTWS CLITEDTGFDLGVTI can also be used for the development of anti-vWF protease antibodies using techniques as known from the art. The development of these antibodies or antibody derivatives or peptidomimetics can be accomplished according methods known to the prior art (Greer J. et al., J. Med. Chem., 1994, Vol. 37, pp. 1035-1054; Harlow E. and Lane D., in "Antibodies. A Laboratory manual", Cold Spring Harbor Laboratory, 1988, Esser C. and Radbruchj A., Annu. Rev. Immunol., 1990, vol. 8, pp 717-735; Kemp D. S., 1990, Trends Biotechnol., pp. 249-255).

The present invention relates also to single polypeptide chains having an apparent molecular weight in reduced SDS-PAGE of between 190 kD and 100 kD, preferably about 180 kD, more preferably about 170 kD, in a particularly preferred embodiment about 160 kD, preferably 120 kD and most preferably about 110 kD, comprising an N-terminal amino acid sequence AAGGILHLELLV. This sequence is preferably directly followed by the sequence AVG, which is then preferably followed by the sequence PDVFQAHQEDTERY VLTNLNIGAELLRDPSLGAQFRVHLVKM-VILTEPEGAPNITANLTSSLLSVCGWSQTINPED DTD-PGHADLVLYITRFDLELPDGN-
RQVRGVTQLGGACSPTWSCLITEDTGFDLGVTI. In contrast to the protease entities described by Furlan et al. (1996) and Tsai (Blood 87(10) (1996), pp. 4235-4244) the vWF multimerase entities according to the present invention are much smaller than the entities described in these documents (around 300 kD (Furlan et al.), and 200 kD (Tsai), respectively).

The proteolytic entities provided with the present invention comprise a physiological vWF cleaving activity which is defined by (1) the cleaving vWF at the peptide bond 842Tyr-843Met, (2) having a direct proteolytic activity which converts vWF having a singlet structure to vWF having a satellite structure, and (3) retaining activity in the presence of a serine protease inhibitor such as diisopropyl fluorophosphate (DFP) and in the presence of a calpain protease inhibitor such as carbobenzyloxy (Z) peptidyl diazomethylketone inhibitor (Z-Leu-Leu-Tyr-$CHN_2$). The proteolytic entities provided with the present invention may also act indirectly via another effector protein, for example a protease.

This single polypeptide chain forms an active vWF cleaving complex together with a metal ion selected from the group consisting $Ca^{++}$, $Sr^{++}$ and $Ba^{++}$. The preferred metal ion is $Ca^{++}$. This active complex is able to cleave vWF in a physiological manner as described above.

A further aspect of the present invention relates to an isolated vWF cleavage complex comprising vWF, a metal ion selected from the group consisting of $Ca^{++}$, $Sr^{++}$ and $Ba^{++}$ and one or more single polypeptide chains having vWF protease activity according to the present invention.

The vWF proteolytic activity (also termed "vWF protease activity") of the peptide chains according to the present invention may be determined by any method described in the art, such as the method according to Furlan et al. (1996), which is preferred for the present invention. Further preferred test systems are described in International Application No. WO 00/50904. The test system described in WO 00/50904 is also suitable for the present vWF protease entities. Alternatively, a collagen binding assay (as described in EP 816 852) can also be used as a test system. Preferably, this test is used for screening and diagnostic purposes.

A further object of the invention is achieved by providing a composition containing the vWF protease according to the invention together with clusterin or an analog or derivative thereof. With relation to the activity of the protein, the term "derivative" or "analog" of clusterin, refers to proteins that show the same proteolytic characteristics as the native clusterin protein.

Clusterin is a heterodimeric glycoprotein consisting of two non-identical subunits, with a molecular mass of approximately 80 kDa (Rosenberg and Silkensen, J., Int. J. Biochem. Cell Biol., 1995, vol. 27, pp. 633-645; Tschopp J. and French, L. E., Clinical and Exp. Immunol., 1994, 97, pp. 11-14). It is produced in a wide array of tissues and found in most biologic fluids. The physiologic functions described in the prior art include complement regulation, lipid transport, sperm maturation, initiation of apoptosis, endocrine secretion, membrane protection and promotion of cell interactions.

It has been found that the unusually high stability of the vWF protease of the present invention in circulating plasma is associated with the presence of clusterin. We have found that the half-life of vWF-cleaving protease activity in vivo is between 1 and 4 days, while other proteases in plasma have half-lives in the range of seconds to hours. The ratio of clusterin to vWF protease in a composition according to the present invention is preferably in a range of 10M:1M to 1M:10M, and more preferably the ratio of clusterin and vWF is in the equimolar range. In human plasma, the concentration of vWF-cleaving protease is 2-10 mg/liter whereas that of clusterin is 50-400 mg/liter plasma (the molar ratio of vWF-cleaving protease to clusterin in human plasma is about 1:20-1:100).

Isolation of the composition from either human plasma or other sources, e.g. supernatants of cell cultures expressing the polypeptide according to the present invention, milk or other body fluids of transgenic animals expressing the polypeptide according to the present invention can be performed by chromatographic means. Preferably, the purification is performed by a combination of chromatographic steps including immunoaffinity chromatography, gel filtration, and ion exchange chromatography. For example, the first purification step can be immunoaffinity chromatography, the second step can be gel filtration, followed by one or more additional immunoaffinity chromatography steps. A further purification can be performed using ion exchange chromatography, preferably anion exchange chromatography and at least one affinity chromatography. Further purification steps can be performed using ion exchange chromatography, gel filtration and further affinity chromatography steps.

As an alternative embodiment, the nucleotide sequence as shown in FIG. 2 can be used for constructing expression systems providing appropriate elements for the expression of the DNA which can then be used for the expression of a polypeptide having vWF protease activity according to the present invention.

The expression vector may comprise, for example, in the direction of transcription, a transcriptional regulatory region and a translational initiation region functional in a host cell, a DNA sequence encoding for the polynucleotide expressing a VWF protease activity according to the present invention and translational and transcriptional termination regions functional in said host cell, wherein expression of said nucleic sequence is regulated by said initiation and termination regions. The expression vector may also contain elements for the replication of said nucleotide. Examples of DNA expression vectors are pBPV, pSVL, pRc/CMV, pRc/RSV, myogenic vector systems (WO 93/09236) or vectors derived from viral systems, for example from vaccinia virus, adenoviruses, adeno-associated virus, herpes viruses, retroviruses or baculo viruses.

The expression vector containing the nucleic acid which encodes the polypeptide having vWF protease activity according to the present invention can be used to transform host cells which then produce said polypeptide. The transformed host cells can be grown in a cell culture system to produce said polypeptide in vitro. The host cells preferably excrete the polypeptide having vWF protease activity into the cell culture medium from which it can be prepared.

The host cells may be cells derived from the body of a mammal, for example fibroblasts, keratinocytes, hematopoietic cells, hepatocytes or myoblasts, which are transformed in vitro with an expression vector system carrying a nucleic acid according to the present invention and re-implanted into the mammal. The polypeptide according to the present invention encoded by said nucleic acid will be synthesized by these cells in vivo and they will exhibit a desired biological activity in the mammal.

The nucleic acid encoding the polypeptide according to the present invention may also be used to generate transgenic animals, which express said polypeptide proteins in vivo. In one embodiment of this specific application, the transgenic animals may express the polypeptide having vWF protease activity in endogenous glands, for example in mammary glands from which the said proteins are secreted. In the case of the mammary glands, said proteins having vWF protease activity are secreted into the milk of the animals from which said proteins can be prepared. The animals may be mice, cattle, pigs, goats, sheep, rabbits or any other economically useful animal.

The vWF protease composition of the present invention can be used, for example, to process recombinantly produced vWF. Recombinant vWF (r-vWF) can be produced in CHO cells, e.g. according to FEBS Letter 375, 259-262 (1995). The r-vWF recovered in this manner is available as a mature vWF and has a singlet structure, i.e. it differs from plasma-derived vWF, which always has a characteristic satellite structure when examined on 2% SDS agarose gels. In International Patent Application No. WO 96/10584 describes that r-vWF is comprised of multimers with high structural integrity which is retained even after purification and treatment for the inactivation of viruses. The intact structure of the r-vWF is defined by a result of electrophoretic analysis consisting of multimer bands with an absence of satellite bands. To prepare an r-vWF preparation having a structure more closely corresponding to that of plasma-derived vWF from r-vWF with singlet structure, r-vWF is treated with the vWF protease composition of the present invention.

According to a further aspect of the present invention, the amino acid sequence and nucleotide sequence as shown in FIG. 2 can also be used for the production of a preparation for the prophylaxis and therapy of diseases that show supranormal vWF content or an increased level of high-molecular weight vWF in patients. This can result in thromboses and thromboembolic diseases. For example, thrombotic throbocytic purpura (TTP), Henoch-Schönlein purpura, preeclampsia, neonatal thrombocytopenia or haemolytic-uremic syndrome. By administering an effective dose of a polypeptide having a vWF protease activity and having an amino acid sequence as shown in FIG. 2, this can lead to reduction of the content of high molecular weight vWF multimers in the patients, resulting in effective therapy of these diseases. The invention is described in the following examples, without being limited thereto.

EXAMPLES

Example 1

Method for Isolating vWF-Cleaving Proteolytic Peptides 1.1. Preparation of an IgG-eTTP coupled affinity gel. The IgG-eTTP was isolated by aid of a 20 ml protein A-Sepharose® (diameter 1.6 cm) in TBS, pH 7.4. Pheresis plasma of a patient suffering from acquired TTP ("erworbenes" TTP; eTTP), which previously had been assayed for its inhibitor content relative to the vWF-cleaving protease was applied to the column in a volume of 50 ml. After subsequent rinsing with TBS, pH 7.4, the bound IgGs were step-wise eluted with citrate, 0.1 M, pH 4.0, and glycine, 0.1 M, pH 2.7. The fractions immediately were brought to a physiological pH by adding Tris, 1.5 M, pH 8.8, and dialysed against TBS, pH 7.4. The Affi-Gel® Hz was coupled according to the producers instructions with the IgG-eTTP which had been washed out of the protein A-Sepharose® with a pH of 4.0. The column material prepared in this manner first was washed as prescribed, subsequently it was washed 3 times alternatingly with 50 ml of buffer B and 200 ml of buffer A (chapter 1.7). Prior to use, intensive rinsing with buffer A was carried out in each instance.

1.2 First Step

As the starting material, 100 ml of pooled CPD plasma which had come from at least three donors and had been stored at −20° C., was used after centrifuging at 2,500 rpm (1,100 g) for 5 min. At a relatively low flow rate (FR: 30 ml/h), the plasma was loaded on a 200 ml chromatographic column with IgG-eTTP Affi-Gel® Hz (hydrazide, diameter 2.6 cm) which had been equilibrated in buffer A. After washing with at least 400 ml of buffer A over night at the same flow rate, a 200 ml desalting gel filtration column (Bio-Gel® P-6DG, diameter 2.6 cm) and a 10 ml protein G-Sepharose® (diameter 1.6 cm), which previously also had been rinsed with buffer A, was connected thereto. After the flow rate had been increased to 100 ml/h, the proteins bound to Affi-Gel Hz were eluted directly with 50 ml of buffer B onto the Bio-Gel® P-6DG so as to remove from the proteins the NaSCN that had been in buffer B. The proteins which had been eluted from the desalting column prior to the NaSCN were led through the protein G Sepharose® without interruption, where they were freed from the IgGs. Here, the flow rate was lowered to 50 ml/h so as to extend the dwell time of the proteins in the 10 ml column. For regeneration, the protein G-Sepharose® was shortly washed with buffer G, and the eluted IgG fraction was stored for analysis.

The first step was carried out 8 times before the collected fractions which had been frozen at −20° C. were pooled and further processed.

1.3 Second Step

The pooled fractions from 8 chromatographies of the first step were diluted 1:1 with $H_2O$ so as to obtain an ionic strength at which the desired proteins would bind to the anion exchange column (High Q Support®). The sample whose volume was from 1,500 to 1,800 ml, depending on the charge used, was checked for its pH and its ionic strength and applied over night at a FR of 90 ml/h through a 50 ml column with Therasorb® (diameter 1.6 cm) onto a 5 ml High Q Support® (diameter 1.6 cm). Both, Therasorb and High Q Support® had previously been equilibrated in buffer D. After washing with approximately 150 ml of buffer D, the Therasorb was disconnected, and the 25 ml Lentil Lectin Sepharose® (diameter 1.6 cm) which had been equilibrated in buffer E was connected to follow the High Q Support®. At a FR of 60 ml/h, the proteins bound to High Q Support were immediately eluted with buffer E directly to the Lentil Lectin-Sepharose®. The proteins which bound to the Lentil Lectin-Sepharose® could be eluted in two steps with buffers G and H and could be collected. The proteins which had remained bound to Therasorb and High Q Support® were washed out with buffer C or buffer F, respectively, and discarded after an analysis.

For regeneration, before being used, the Lentil Lectin-Sepharose® in each case was rinsed according to the producer's instruction 3 times alternatingly with 20 ml each of buffers I and J, the High Q Support was rinsed successively with 10 ml each of NaOH 1N and NaCl 1M.

1.4 Third Step

The pooled fractions which had been eluted from the Lentil Lectin-Sepharose® with buffer H were dialysed three times for a total of 4 h, each against 1 l of buffer D, and again applied to the High Q Support at a flow rate of 60 ml/h. Connected thereinfront was a 5 ml heparin-Sepharose (diameter 1.4 cm), which likewise had been equilibrated in buffer D. After the application of the sample, it was rinsed with approximately 50 ml of buffer D, the heparin-Sepharose was disconnected, and a 500 ml Sephacryl® S-300 HR (diameter 2.6 cm), which had been equilibrated in buffer L, was connected thereto. The proteins bound to High Q Support were directly eluted to the gel filtration column with 10 ml of buffer K. The exclusion chromatography was effected at a flow rate of 42 ml/h, and the fractions were collected at 7 ml each. The proteins which were more strongly bound to High Q Support® were again eluted with buffer F, those which remained adhered to the heparin-Sepharose, with buffer K.

1.5 Fourth Step

The pool of the active fractions from the third step was applied without treatment at a FR of 10 ml/h to a 1 ml anti-$\alpha_2$-macroglobulin column (flow rate 0.7 cm) which had been equilibrated in buffer L. The anti-$\alpha_2$-macroglobulin column was prepared by immobilization according to the instructions, of rabbit-anti-$\alpha_2$-macroglobulin antibodies at a concentration of 4.9 mg/ml on CNBr-activated Sepharose. The proteins bound thereon were eluted with NaSCN 3M in buffer L and with buffer C and stored for analysis.

1.5. Materials

| buffer | Composition | Concentration | pH |
|---|---|---|---|
| buffer A | Tris | 10 mM | pH 7.4 |
| | NaCl | 0.15 M | |
| | Na$_3$-citrate | 1 mM | |
| | Na acid | 0.02% | |
| buffer B | NaSCN in buffer A | 3.0M | pH 7.4 |
| buffer C | glycine | 0.1M | pH 2.7 |
| | Na acid | 0.02% | |
| buffer D | Tris | 10 mM | pH 7.4 |
| | NaCl | 75 mM | |
| buffer E | Tris | 20 mM | pH 7.4 |
| | NaCl | 0.5M | |
| | MnCl$_2$ | 1 mM | |
| buffer F | Tris | 10 mM | pH 7.4 |
| | NaCl | 1.0M | |
| buffer G | Tris | 20 mM | pH 7.4 |
| | NaCl | 0.5M | |
| | Methyl-$\alpha$-D-mannopyranoside | 30 mM | |
| buffer H | Tris | 20 mM | pH 7.4 |
| | NaCl | 0.5M | |
| | Methyl-$\alpha$-D-mannopyranoside | 0.3M | |
| buffer I | Tris | 20 mM | pH 8.5 |
| | NaCl | 0.5M | |
| buffer J | Na acetate | 20 mM | pH 5.5 |
| | NaCl | 0.5M | |
| buffer K | Tris | 10 mM | pH 7.4 |
| | NaCl | 0.5M | |
| buffer L (TBS) | Tris | 10 mM | pH 7.4 |
| | NaCl | 0.15M | |

Chromatographic Materials

| Material | Source |
|---|---|
| affi-gel hydrazide gel ®: for immobilizing specific IgG's | Bio-Rad, Hercules, CA, USA |
| anti-$\alpha_2$-macroglobulin column: isolation of $\alpha_2$-macroglobulin | applicant's own production (see 1.5): rabbit-anti-human-$\alpha_2$-macroglobulin antibody on CNBr activated Sepharose 4B; 4.9 mg/ml |
| Bio-Gel ® P6-DG, medium: gel filtration with exclusion limit ≥6 kDa | Bio-Rad |
| CNBr activated Sepharose 4B ®: for mmobilizing proteins | Amersham Pharmacia Biotech, Uppsala, S |
| heparin Sepharose, HITrap ® 5 ml: affinity chromatography: binds various proteins | Amersham Parmacia |
| High Q Support ®, Macro-Prep: strong anion exchanger | Bio-Rad |
| IgG-eTTP Affi-gel Hz: for binding vWF-protease | applicant's own production (see 1.1.): IgG-eTTP on Affi-gel Hz hydrazide |
| Lentil Lectin-Sepharose 4B: affinit chromatography: binds to sugar residues o proteins | Amersham Pharmacia |
| protein A Sepharose ® CL-4B. binds IgG of type 1, 2 and 4 | Amersham Pharmacia |
| protein G Sepharose ® 4FF: isolation of IgGs of all types | Amersham Pharmacia |
| Sephacryl ® S-300 HR: gel filtration for MWs 10,000 to 1,500,000 | Amersham Pharmacia |
| Therasorb: coupled with sheep-anti-human-Ig antibodies: isolation of human immunoglobulins | Serag-Wiessner, Naila, D |

1.6 Fifth Step

Alternatively, or in addition to step four, an anti-clusterin column chromatography as a further step can be applied. The samples were prepared identically to the anti-$\alpha$2-macroglobulin-column using anti-clusterin antibodies.

2. SDS-Page Reduced/Non-Reduced

SDS-Polyacrylamide Gel-Electrophoresis (SDS-PAGE)

SDS-PAGE was done according to Lämmli. The separating gels were prepared having a size of 13.5 cm height, 15 cm width and 3 mm thickness, having the composition as follows:

Concentration of SDS-Polyacrylamide Gel for a Gradient Gel of 4% to 12%:

| | 4% | 12% |
|---|---|---|
| Acrylamide | 4% | 12% |
| N,N'-Methylenebisacrylamide | 0.107% | 0.32% |
| Tris (Tris(hydroxymethyl)aminomethane) | 0.4M | 0.4M |
| APS (Ammoniumperoxydisulfate) | 0.03% | 0.03% |
| SDS (Sodium Dodecyl Sulfate) | 0.1% | 0.1% |
| Temed (N,N,N',N'-Tetramethylethylenediamine) | 0.067% | 0.067% |
| | pH 8.7 | pH 8.7 |

30 ml of each of the 4% and 12% solutions were poured between two glass plates.

After polymerization, the stacking gel was prepared, having a height of 3 cm and having 16 slots. The volume of each slot was 150 µl.

Stacking Gel:

| | |
|---|---|
| Acrylamide | 3% |
| N,N'-Methylenebisacrylamide | 0.08% |
| Tris | 0.1M |
| APS | 0.03% |
| SDS | 0.1% |
| Temed | 0.2% |
| | pH 6.8 |

100 µl probe were mixed with 50 µl buffer for the SDS-PAGE and incubated 20 minutes at 60° C. Probes that had to be reduced were mixed with DTT (1,4-Dithio-DL-threitol), 65 mM before the solution was heated up.

Buffer for the SDS-PAGE:

| | |
|---|---|
| Tris | 0.15M |
| SDS | 4% |
| Glycerin-87% | 30% |
| Bromine phenol blue few amounts | |
| | pH 6.8 |

After heating, the probes were centrifuged, loaded onto the slots of the SDS PAG and covered with electrophoresis buffer. Electrophoresis was run over night in a vertical chamber system, using 60 V voltage.

Electrophoresis Buffer:

| | |
|---|---|
| Tris | 50 mM |
| Glycine | 0.38M |
| EDTA (Titriplex III: ethylen-dinitrilo tetra acetic acid-disodium salt -dihydrate) | 2 mM |
| SDS | 0.1% |
| | standard-pH 8.3 |

Silver Staining:

The gels (13.5×15×0.3 cm) were put into a tray containing a mixture of methanol (25%), acetic acid (7.5%), water (65.5%) and glycerin-87% (2%) (fixing solution) for at least 3 hours. Subsequently, the gels were rinsed 4-times with 200 ml water for 1 hour. Then the gel was put into a sodium thio sulfate solution (0.02%), washed twice with water (1 min) and incubated 2-times 20 minutes with silver nitrate (0.1%) in water under constant shaking.

After rinsing with water for two times, the gel was shaken in a developing solution, consisting of sodium carbonate (2.5%) and formaldehyde-37% (0.04%) in water. The reaction was stopped with the fixing solution, as soon as the proteins were visible as gray to brown bands.

Example 2

Affinity Purification of von Willebrand Factor (vWF)

The peptide with the sequence AAGGILHLELLV was synthesized on a solid-phase support following the method of Barany, G and Merrifield, R. B. (1980) Solid-phase Peptide Synthesis, in *The Peptides* vol. 2 (Gross, E. and Meienhofer, J., eds) Academic, New York. After cleavage and de-protection of the peptide, the peptide was purified by ion-exchange chromatography. The peptide was characterized by reverse phase HPLC on a C8 silica column with gradient elution in trifluoro acetic acid with acetonitrile. The peptide showed no major byproducts.

The peptide was solubilized in a concentration of 5 mg/mL in 0.1 molar phosphate buffer pH 7.5 and incubated with a pre-activated gel suitable for affinity chromatography (Actigel, ALD-Superflow, Sterogene). Prior to coupling of the peptide to the gel the pre-activated matrix was excessively washed with the same phosphate buffer. One volume of the pre-washed gel was then mixed with one volume of the peptide solution to be immobilized and subsequently 0.1 volume portions of a solution of 0.1 molar cyanoborohydride (NaCNBH$_3$) in 0.1 molar phosphate buffer pH 7.5. The gel was suspended in this solution and shaked for 15 hours at room temperature. Subsequently the gel was washed on a sinter funnel with a 10-fold volume of the phosphate buffer containing 150 mmolar NaCl and with 5 volumes of the phosphate buffer containing 2 molar NaCl. Then the gel was equilibrated with an access of 0.1 molar phosphate buffer pH 7.0.

The gel was then transferred into a chromatographic column having a dimension of diameter to gel bed height of 1:4. By determining the peptide concentration the solution of the incubation supernatant after separation from the gel and the washing solutions the amount of peptide coupled to the affinity matrix was calculated. The coupling rate was 85%.

The gel was subsequently used to purify vWF from a Factor VIII (FVIII)/vWF complex. A FVIII/vWF complex concentrate was produced according to EP 0 270 516 containing vWF in a concentration of 260 U vWF:Ag/ml and a specific activity of 13.5 U vWF:Ag/mg Protein. The concentrate was diluted with 20 mM phosphate buffer pH 7.0 to a final vWF concentration of 6 U vWF:Ag/mL. A volume of 20 ml of this solution was subjected to the affinity column with immobilized peptide described above. After washing the column with 10 ml of the phosphate buffer the vWF specifically bound to the peptide ligand was eluted by a linear gradient from 0-2 mol/l NaCl in phosphate buffer at a flow rate of 1 ml/minute. Fractions of 1 ml were collected and their optical density was determined at 280 nm. All fractions were measured for their content of vWF antigen determined by a specific ELISA method (Asserachrom vWF, Boehringer, Mannheim). Measurement showed a specific peak of vWF eluting from the peptide at a NaCl concentration of 100 mmol/l, while most of the protein measured by UV-absorption eluted prior to the vWF fraction with the washing buffer. The vWF containing fractions were pooled and measured for vWF activity. The vWF in this pool had a specific activity of 95 U vWF/mg protein and was essentially free from other proteins.

Example 3

Anti-Peptide Antibodies

The peptide with the sequence AAGGILHLELLV was synthesized and purified as described in example 2. The peptide was then used to immunize 3 months old BALB/c mice with the following protocol: A primary subcutaneous injection of 100 µg peptide antigen emulsified in Freund's complete adjuvant in 100 µl followed by intra-peritoneal boosts of 100 µg peptide antigen in phosphate buffered saline at monthly intervals.

The anti-peptide titer was tested by routine ELISA method using purified peptide as screening antigen. After the final boost the spleens were taken from the mice for cell fusion. Cell fusion was carried out according to a standard protocol originally described by Kohler G. and Milstein C. 1975, Nature 256:495. Anti-peptide antibodies producing hybridoma cell lines were screened by standard techniques with the purified peptide as screening antigen essentially based on a conventional ELISA methodology. After cloning a cell line could be isolated with a high expression level of an antibody specific for the screening peptide with the sequence AAGGILHLELLV. This cell line was cultured on serum-free culture medium and grown to high density. The supernatant of the cell culture was harvested by centrifugation to remove cells and the monoclonal antibody containing supernatant was concentrated by ultra-diafiltration and conditioned for further use.

The monoclonal antibody obtained had a high selectivity for the vWF cleaving protease as described by Furlan et al. 1996, Blood 87:4223-4234. This monoclonal antibody was immobilized to a polystyrene ELISA plate in a carbonate/bicarbonate buffer, 0.05 molar, pH 9.6, at a concentration of 5 µg immunoglobuline/ml overnight (16 hours) at 4° C., with each 100 µl of coating solution per well. The coating solution was removed from the wells and replaced by a solution of bovine serum albumin (BSA) at a concentration of 100 µg/ml at a volume of 100 µL per well, for 2 hours. The BSA solution was removed and the wells were washed with phosphate buffered saline. The pre-coated plates were then incubated with either samples of platelet poor plasma from healthy human plasma donors or platelet poor plasma from patients with an unclear diagnosis of either thrombotic thrombocytopenic purpura (TTP) or hemolytic uremic syndrome (HUS). After incubation of the plasma samples with the antibody coated ELISA plates as in a routine sandwich ELISA system, after 3 hours the plasma was removed from the wells. Wells were washed with phosphate buffered saline and incubated with the monoclonal antibody directed against the peptide with the sequence AAGGILHLELLV, conjugated with horse radish peroxidase following the method of Wilson, M. B. and Nakane, P. K (1978) In *Immunofluorescence and Related Staining Techniques*. Knapp, W. Holubar, K. and Wick, G (eds), Elsevier/North Holland, Amsterdam, p. 215, and detected by the OPT reagent as described by Cathy D. and Raykundalia Ch. (1989) ELISA and related enzyme immunoassays, in *Antibodies II a practical approach*. Cathy D (ed), IRL Press Eynsham Oxford England, p. 97.

Based on the level of the samples from the healthy human plasma donors a normal range was established. Plasmas from patients with HUS had a vWF protease activity equivalent to healthy humans while patients with TTP had a decreased protease activity as confirmed by an assay based on a different assay principle as described in WO00/509904.

Example 4

Amino Acid Sequencing and Amino Acid Analysis of the vWF Protease

The final protein preparation from the third step of isolation was electrophoresed on a 1.5 mm-thick SDS-polyacrylamide gel according to Laemmli (Laemmli U K., Nature, 1970, 227, pp. 680-685) A gradient of 4 to 12% polyacrylamide was used for fractionation of high molecular weight proteins, and a gradient of 8 to 12% polyacrylamide for low molecular weight proteins. After electrophoresis under non-reducing or reducing conditions (final concentration 65 mmol/l dithiotreitol), the proteins were blotted onto PVDF-membranes and stained for 2 min with 0.25% Coomassie Blue in 45% methanol, 9% acetic acid and 46% H$_2$O. After rinsing with a mixture of 50% methanol, 10% acetic add and 40% H$_2$O, the visible protein bands were cut out and analyzed on a Procise-cLC Sequencer (Foster City, Calif.) at the Chemical Institute of the University of Bern.

The N-terminal amino acid sequence of polypeptide bands separated by SDS-PAGE of purified vWF-cleaving protease is shown in table 1:

| Molecular weight | Amino Acid sequence |
|---|---|
| 350 kDa unreduced | Ser-Val-Ser-Gly-Lys-Pro-Gln-Tyr-Met-Val* |
| 150 kDa unred. | Ala-Ala-Gly-Gly-Ile |
| 140 kDa unred. | Ala-Ala-Gly-Gly-Ile |
| 130 kDa unred. | Ala-Ala-Gly-Gly-Ile |
| 110 kDa unred. | Ala-Ala-Gly-Gly-Ile-Leu-His-Leu-Glu |
| 70 kDa unred. | Asp/Ser-Gln/Leu-Thr/Met-Val/Pro-Ser/Phe** |
| 180 kDa reduced | Ala-Ala-Gly-Gly-Ile-Leu-His-Leu-Glu |
| 170 kDa reduced | Ala-Ala-Gly-Gly-Ile |
| 160 kDa reduced | Ala-Ala-Gly-Gly-Ile-Leu-His-Leu-Glu-Leu-Leu-Val-Ala-Val-Gly |
| 120 kDa reduced | Ala-Ala-Gly-Gly-Ile-Leu-His-Leu-Glu-Leu-Leu-Val-Ala-Val-Gly |
| 40 kDa reduced | Asp-Gln-Thr-Val-Ser** |

*identified as α2-macroglobulin
**identified as clusterin

Analysis of the composition of the amino acids was performed from the same sample as used for amino acid sequencing. The protein bands were hydrolyzed in the gas phase over 6 N HCl for 22 hours at 110° C. and the amino acids were determined by high performance liquid chromatography.

Four unreduced polypeptide bands from SDS-PAGE of purified vWF-cp with M$_r$ 150, 140, 130, and 110 kDa were analyzed The results are shown in Tab. 2:

| | No. residues/100 residues | | | |
|---|---|---|---|---|
| Amino acid | 150 kDa | 140 kDa | 130 kDa | 110 kDa |
| Asx | 6.7 | 7.0 | 7.4 | 8.3 |
| Glx | 12.2 | 12.0 | 12.8 | 11.8 |
| Ser | 8.4 | 8.9 | 8.8 | 9.2 |
| Gly | 11.8 | 12.1 | 12.1 | 12.9 |
| His | 2.5 | 2.3 | 2.5 | 2.4 |
| Arg | 8.3 | 7.6 | 8.1 | 7.2 |
| Thr | 5.6 | 5.5 | 5.6 | 5.7 |
| Ala | 10.1 | 9.5 | 9.6 | 8.2 |
| Pro | 8.9 | 8.5 | 8.3 | 8.1 |
| Tyr | 2.1 | 2.7 | 2.3 | 2.4 |
| Val | 7.0 | 6.9 | 6.7 | 6.5 |
| Ile | 2.7 | 2.9 | 2.6 | 3.0 |
| Leu | 10.0 | 9.9 | 9.1 | 9.7 |
| Phe | 2.6 | 2.8 | 2.6 | 3.2 |
| Lys | 1.0 | 1.3 | 1.3 | 1.4 |

Example 5

Search on Chromosome 9 Clone RP11-224N20 for Potential Exons of the vWF-Protease The coding region of the N-terminus of the activated vWF protease (aminoacids A-A-G-G-I-L-H-L-E-L-L-V-A-V-G) was found on Chromosome 9 clone RP11-224N20 bases 156653 to 156697. Thus the nucleotide sequence from base 150001 to 185911 was screened for potential exons. Consecutive overlapping genome-segments with various lengths (1500 bases-5000 bases) were analysed using search engines that were queried via the internet-explorer. The genomic sequence segments, its translations and the results of the search were managed using the 'Vectors NTI Suite1 v.5.2' computer-program (Informax Inc., USA).

The first four exons of the search were translated into the corresponding amino acid sequence and these sequences were searched for homologies. This search revealed that each sequence displays high homology with the amino acid sequence of the family of human disintegrin and metalloproteinases with thrombospondin motifs (ADAM-TS).

By alignments performed with the 'Vectors NTI Suite1 v.5.2-AlignX' program (Informax Inc., USA), further potential exons were identified that encode for amino acid sequences that are homologous to segments of the human ADAM-TS sequences. Exons potentially encoding for the entire proteinase domain, for parts of the disintegrin like domain, the thrombospondin motif, the cystein-rich domain, as well as for three potential thrombospondin submotifs of a new ADAM-TS proteinase were thus identified. The succession of the exons on the genomic sequence was found to be consistant with the succession of the corresponding amino acid segments on the ADAM-TS consensus sequence.

Example 6

Cloning of the Gene Expressing the vWF-Protease Gene

Human salivary gland poly A+ RNA was purchased from Clontech. First strand cDNA was obtained using Expand reverse transcriptase (Roche) and oligo d(T) primer according to the manufacturer's instructions. PCR was performed using 5'CGGCGGGATCCTACACCTGG 3' and 5'AATGGTGACTCCCAGGTCGA 3' as primers with 10 ng of salivary gland cDNA as template and 10 U of Hot Star Taq polymerase (Quiagen). The thermal cycling parameters were an initial incubation at 94° C. for 15 minutes followed by 45 cycles of 94° C. (50 sec), 50° C. (50 sec), 72° C. (2 min). PCR products were directly sequenced in both directions using the BigDye Terminator Cycle Sequencing Ready Reaction Kit (Perkin-Elmer Life Science).

The obtained DNA sequence was used to scan the genomic data base using BLAST (basic local alignment search tool) programs and matched to the chromosome 9 clone RP11-224N20 DNA sequence was translated to amino acids sequence using ExPASy proteomic tools. The DNA and translated amino acid sequences corresponding to 4 putative exons of chromosome 9q34 are shown in FIG. 2.

---

The invention claimed is:

1. A method for detection of vWF protease polypeptide in a sample comprising plasma, comprising the steps of:
   (a) contacting the sample with a monoclonal antibody that binds to a polypeptide exhibiting vWF protease activity that comprises at least one single isolated peptide chain that is present in human plasma and has a molecular weight from about 180 kD to about 120 kD as determined by SDS-PAGE under reducing conditions and comprises the amino acid sequence AAGGILHLELLV (SEQ ID NO: 1); and
   (b) detecting the complex, thereby detecting vWF protease polypeptide.

2. The method according to claim 1, wherein the polypeptide to which the antibody binds comprises the amino acid sequence:
   AAGGILHLELLVAVGPDVFQAHQED-TERYVLTNLNIGAELLRDPSLGAQ-FRVHLVKMVILTEPEG APNITANLTSSLLSVCG-WSQTINPEDDTDPGHADLVLYITRFDLELPDGN-RQVRGVTQLGGACS PTWSCLITEDTGFDLGVTI (SEQ ID NO:4).

3. The method according to claim 1, wherein the antibody binds to the amino acid sequence AAGGILHLELLV.

4. The method according to claim 1, wherein the polypeptide to which the antibody binds has a molecular weight of about 170 kD.

5. The method according to claim 1, wherein the polypeptide to which the antibody binds has a molecular weight of about 160 kD.

6. The method according to claim 1, wherein the polypeptide to which the antibody binds has a molecular weight of about 120 kD.

* * * * *

UNITED STATES PATENT AND TRADEMARK OFFICE
CERTIFICATE OF CORRECTION

PATENT NO. : 8,703,429 B2  
APPLICATION NO. : 12/171934  
DATED : April 22, 2014  
INVENTOR(S) : Bernhard Laemmle et al.

Page 1 of 1

It is certified that error appears in the above-identified patent and that said Letters Patent is hereby corrected as shown below:

Title Page, Item (73) should read:

-- (73) Assignee: Baxter Innovations GmbH, Vienna (AT) --

In the Claims

Column 23, claim 2, line 17-22 should read as follows:

-- AGGILHLELLVAVGPDVFQAHQEDTERYVLTNLNIGAELLRDPSLGAQFRVHLVK
MVILTEPEGAPNITANLTSSLLSVCGWSQTINPEDDTDPGHADLVLYITRFDLELP
DGNRQVRGVTQLGGACSPTWSCLITEDTGFDLGVTI (SEQ ID NO:4) --

Signed and Sealed this  
Twenty-ninth Day of July, 2014

Michelle K. Lee  
*Deputy Director of the United States Patent and Trademark Office*

UNITED STATES PATENT AND TRADEMARK OFFICE
CERTIFICATE OF CORRECTION

| | | |
|---|---|---|
| PATENT NO. | : 8,703,429 B2 | Page 1 of 1 |
| APPLICATION NO. | : 12/171934 | |
| DATED | : April 22, 2014 | |
| INVENTOR(S) | : Laemmle et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 688 days.

Signed and Sealed this
Eighth Day of September, 2015

Michelle K. Lee
*Director of the United States Patent and Trademark Office*

SEQUENCE LISTING

<160> NUMBER OF SEQ ID NOS: 15

<210> SEQ ID NO 1
<211> LENGTH: 12
<212> TYPE: PRT
<213> ORGANISM: human

<400> SEQUENCE: 1

Ala Ala Gly Gly Ile Leu His Leu Glu Leu Leu Val
1               5                   10

<210> SEQ ID NO 2
<211> LENGTH: 133
<212> TYPE: PRT
<213> ORGANISM: human

<400> SEQUENCE: 2

Pro Asp Val Phe Gln Ala His Gln Glu Asp Thr Glu Arg Tyr Val Leu
1               5                   10                  15

Thr Asn Leu Asn Ile Gly Ala Glu Leu Leu Arg Asp Pro Ser Leu Gly
            20                  25                  30

Ala Gln Phe Arg Val His Leu Val Lys Met Val Ile Leu Thr Glu Pro
        35                  40                  45

Glu Gly Ala Pro Asn Ile Thr Ala Asn Leu Thr Ser Ser Leu Leu Ser
    50                  55                  60

Val Cys Gly Trp Ser Gln Thr Ile Asn Pro Glu Asp Asp Thr Asp Pro
65                  70                  75                  80

Gly His Ala Asp Leu Val Leu Tyr Ile Thr Arg Phe Asp Leu Glu Leu
                85                  90                  95

Pro Asp Gly Asn Arg Gln Val Arg Gly Val Thr Gln Leu Gly Gly Ala

-continued

```
                  100                 105                 110
Cys Ser Pro Thr Trp Ser Cys Leu Ile Thr Glu Asp Thr Gly Phe Asp
        115                 120                 125

Leu Gly Val Thr Ile
        130

<210> SEQ ID NO 3
<211> LENGTH: 444
<212> TYPE: DNA
<213> ORGANISM: human

<400> SEQUENCE: 3
gctgcaggcg gcatcctaca cctggagctg ctggtggccg tgggccccga tgtcttccag    60
gctcaccagg aggacacaga gcgctatgtg ctcaccaacc tcaacatcgg ggcagaactg   120
cttcgggacc cgtccctggg ggctcagttt cgggtgcacc tggtgaagat ggtcattctg   180
acagagcctg agggtgcccc aaatatcaca gccaacctca cctcgtccct gctgagcgtc   240
tgtgggtgga gccagaccat caaccctgag gacgacacgg atcctggcca tgctgacctg   300
gtcctctata tcactaggtt tgacctggag ttgcctgatg gtaaccggca ggtgcgggcc   360
gtcacccagc tgggcggtgc ctgctcccca acctggagct gcctcattac cgaggacact   420
ggcttcgacc tgggagtcac catt                                          444

<210> SEQ ID NO 4
<211> LENGTH: 148
<212> TYPE: PRT
<213> ORGANISM: human

<400> SEQUENCE: 4

Ala Ala Gly Gly Ile Leu His Leu Glu Leu Leu Val Ala Val Gly Pro
 1               5                  10                  15

Asp Val Phe Gln Ala His Gln Glu Asp Thr Glu Arg Tyr Val Leu Thr
                20                  25                  30

Asn Leu Asn Ile Gly Ala Glu Leu Leu Arg Asp Pro Ser Leu Gly Ala
            35                  40                  45

Gln Phe Arg Val His Leu Val Lys Met Val Ile Leu Thr Glu Pro Glu
        50                  55                  60

Gly Ala Pro Asn Ile Thr Ala Asn Leu Thr Ser Ser Leu Leu Ser Val
 65                  70                  75                  80

Cys Gly Trp Ser Gln Thr Ile Asn Pro Glu Asp Asp Thr Asp Pro Gly
                85                  90                  95

His Ala Asp Leu Val Leu Tyr Ile Thr Arg Phe Asp Leu Glu Leu Pro
            100                 105                 110

Asp Gly Asn Arg Gln Val Arg Gly Val Thr Gln Leu Gly Gly Ala Cys
        115                 120                 125

Ser Pro Thr Trp Ser Cys Leu Ile Thr Glu Asp Thr Gly Phe Asp Leu
    130                 135                 140

Gly Val Thr Ile
145

<210> SEQ ID NO 5
<211> LENGTH: 15
<212> TYPE: PRT
<213> ORGANISM: human

<400> SEQUENCE: 5

Ala Ala Gly Gly Ile Leu His Leu Glu Leu Leu Val Ala Val Gly
 1               5                  10                  15
```

```
<210> SEQ ID NO 6
<211> LENGTH: 150
<212> TYPE: PRT
<213> ORGANISM: human

<400> SEQUENCE: 6

Arg Arg Ala Ala Gly Gly Ile Leu His Leu Glu Leu Val Ala Val
1               5                   10                  15

Gly Pro Asp Val Phe Gln Ala His Gln Glu Asp Thr Glu Arg Tyr Val
                20                  25                  30

Leu Thr Asn Leu Asn Ile Gly Ala Glu Leu Leu Arg Asp Pro Ser Leu
            35                  40                  45

Gly Ala Gln Phe Arg Val His Leu Val Lys Met Val Ile Leu Thr Glu
        50                  55                  60

Pro Glu Gly Ala Pro Asn Ile Thr Ala Asn Leu Thr Ser Ser Leu Leu
65                  70                  75                  80

Ser Val Cys Gly Trp Ser Gln Thr Ile Asn Pro Glu Asp Thr Asp
                        85                  90                  95

Pro Gly His Ala Asp Leu Val Leu Tyr Ile Thr Arg Phe Asp Leu Glu
                100                 105                 110

Leu Pro Asp Gly Asn Arg Gln Val Arg Gly Val Thr Gln Leu Gly Gly
                115                 120                 125

Ala Cys Ser Pro Thr Trp Ser Cys Leu Ile Thr Glu Asp Thr Gly Phe
            130                 135                 140

Asp Leu Gly Val Thr Ile
145                 150

<210> SEQ ID NO 7
<211> LENGTH: 10
<212> TYPE: PRT
<213> ORGANISM: human

<400> SEQUENCE: 7

Ser Val Ser Gly Lys Pro Gln Tyr Met Val
1               5                   10

<210> SEQ ID NO 8
<211> LENGTH: 5
<212> TYPE: PRT
<213> ORGANISM: human

<400> SEQUENCE: 8

Ala Ala Gly Gly Ile
1               5

<210> SEQ ID NO 9
<211> LENGTH: 9
<212> TYPE: PRT
<213> ORGANISM: human

<400> SEQUENCE: 9

Ala Ala Gly Gly Ile Leu His Leu Glu
1               5

<210> SEQ ID NO 10
<211> LENGTH: 10
<212> TYPE: PRT
<213> ORGANISM: human

<400> SEQUENCE: 10
```

```
Asp Ser Gln Leu Thr Met Val Pro Ser Phe
1               5                   10
```

<210> SEQ ID NO 11
<211> LENGTH: 15
<212> TYPE: PRT
<213> ORGANISM: human

<400> SEQUENCE: 11

```
Ala Ala Gly Gly Ile Leu His Leu Glu Leu Leu Val Ala Val Gly
1               5                   10                  15
```

<210> SEQ ID NO 12
<211> LENGTH: 5
<212> TYPE: PRT
<213> ORGANISM: human

<400> SEQUENCE: 12

```
Asn Gln Thr Val Ser
1               5
```

<210> SEQ ID NO 13
<211> LENGTH: 20
<212> TYPE: DNA
<213> ORGANISM: oligo primer

<400> SEQUENCE: 13
cggcgggatc ctacacctgg                                                    20

<210> SEQ ID NO 14
<211> LENGTH: 20
<212> TYPE: DNA
<213> ORGANISM: oligo primer

<400> SEQUENCE: 14
aatggtgact cccaggtcga                                                    20

<210> SEQ ID NO 15
<211> LENGTH: 136
<212> TYPE: PRT
<213> ORGANISM: human

<400> SEQUENCE: 15

```
Ala Val Gly Pro Asp Val Phe Gln Ala His Gln Glu Asp Thr Glu Arg
1               5                   10                  15

Tyr Val Leu Thr Asn Leu Asn Ile Gly Ala Glu Leu Leu Arg Asp Pro
                20                  25                  30

Ser Leu Gly Ala Gln Phe Arg Val His Leu Val Lys Met Val Ile Leu
            35                  40                  45

Thr Glu Pro Glu Gly Ala Pro Asn Ile Thr Ala Asn Leu Thr Ser Ser
        50                  55                  60

Leu Leu Ser Val Cys Gly Trp Ser Gln Thr Ile Asn Pro Glu Asp Asp
65                  70                  75                  80

Thr Asp Pro Gly His Ala Asp Leu Val Leu Tyr Ile Thr Arg Phe Asp
                85                  90                  95

Leu Glu Leu Pro Asp Gly Asn Arg Gln Val Arg Gly Val Thr Gln Leu
            100                 105                 110

Gly Gly Ala Cys Ser Pro Thr Trp Ser Cys Leu Ile Thr Glu Asp Thr
        115                 120                 125

Gly Phe Asp Leu Gly Val Thr Ile
    130                 135
```